United States Patent [19]

Chabert et al.

[11] Patent Number: 5,665,886
[45] Date of Patent: Sep. 9, 1997

[54] SALTS OF SUBSTITUTED NITROGENOUS HETEROAROMATIC COMPOUNDS, A PROCESS FOR THEIR PREPARATION AND PHARMACEUTICAL COMPOSITIONS CONTAINING THEM

[75] Inventors: Nathalie Chabert, Cournonterral; Xavier Emonds-Alt, Combaillaux; Vincenzo Proietto, Saint Georges d'Orques; Didier Van Broeck, Montpellier, all of France

[73] Assignee: Sanofi, France

[21] Appl. No.: 545,772

[22] PCT Filed: Mar. 24, 1995

[86] PCT No.: PCT/FR95/00368

§ 371 Date: Nov. 24, 1995

§ 102(e) Date: Nov. 24, 1995

[87] PCT Pub. No.: WO95/26339

PCT Pub. Date: Oct. 5, 1995

[30] Foreign Application Priority Data

Mar. 25, 1994 [FR] France .................................. 94 03561

[51] Int. Cl.$^6$ ........................ C07D 213/38; C07D 213/36
[52] U.S. Cl. .......................... 546/300; 546/301; 546/312; 546/337
[58] Field of Search ................................. 546/300, 301, 546/312, 337

[56] References Cited

U.S. PATENT DOCUMENTS 5,340,822  8/1994  Emonds-Alt ........................... 514/316

FOREIGN PATENT DOCUMENTS

A-0 512 901  11/1992  European Pat. Off. .
A-0 559 538   9/1993  European Pat. Off. .
A-0 591 040   4/1994  European Pat. Off. .

OTHER PUBLICATIONS

Maggi et al., *J. Auton. Pharmacol.*, vol. 13, 1993, pp. 23–93.

*Primary Examiner*—C. Warren Ivy
*Assistant Examiner*—D. Margaret M. Mach
*Attorney, Agent, or Firm*—Bacon & Thomas

[57] ABSTRACT

The invention concerns compounds of formula:

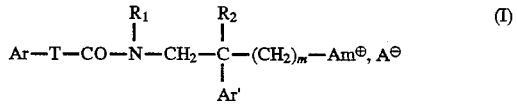

in which $Am^+$ represents a substituted 1-pyridylium radical, a substituted 3-thiazolylium radical, a substituted 1-pyridazinylium radical or a substituted 3-imidazolylium radical, and their salts with mineral or organic acids, whether in their optically pure or racemic form. The invention also concerns a process for the preparation of these compounds and pharmaceutical compositions containing them. Activity: antagonists of neurokinin receptors.

11 Claims, No Drawings

SALTS OF SUBSTITUTED NITROGENOUS HETEROAROMATIC COMPOUNDS, A PROCESS FOR THEIR PREPARATION AND PHARMACEUTICAL COMPOSITIONS CONTAINING THEM

This application is a 371 of PCT/FR95/00368, filed on 24 Mar. 1995, published as WO95/26339 Oct. 5, 1995.

The present invention relates to novel salts of substituted nitrogenous heteroaromatic compounds, a process for their preparation and pharmaceutical compositions containing them as active ingredients.

More particularly, the present invention concerns a novel class of salts of substituted nitrogenous heteroaromatic compounds for therapeutic use in pathological phenomena which involve the tachykinin system, non limiting and exclusive examples of which are: pain (D. Regoli et al., Life Sciences, 1987, 40, 109–117), allergy and inflammation (J. E. Morlay et al., Life Sciences, 1987, 41, 527–544), circulatory insufficiency (J. Losay et al., 1977, Substance P, Von Euler, I. S. and Pernow ed., 287–293, Raven Press, New York), gastrointestinal problems (D. Regoli et al., Trends Pharmacol. Sci., 1985, 4, 481–484), respiratory problems (J. Mizrahi et al., Pharmacology, 1982, 25, 39–50), neurological problems, neuropsychiatric problems (C. A. Maggi et al., J. Autonomic Pharmacol., 1993, 13, 23–93).

A number of studies have recently been carried out on tachykinins and their receptors. Tachykinins are distributed in both the central nervous system and in the peripheral nervous system. Receptors for tachykinins have been recognised and classified into three types: $NK_1$, $NK_2$, and $NK_3$. Substance P (SP) is the endogenous ligand of $NK_1$ receptors, neurokinin A ($NK_A$) is that of $NK_2$ receptors and neurokinin B ($NK_B$) is that of $NK_3$ receptors.

Receptors $NK_1$, $NK_2$ and $NK_3$ have been shown to exist in different species. A review by C. A. Maggi et al. summarises this for tachykinins receptors and their antagonists and discusses pharmacological studies and applications to human therapeutics (J. Autonomic Pharmacol., 1993, 13, 23–93).

Among specific antagonists for receptor $NK_1$ the following non peptide compounds may be cited: CP-96345 (J. Med. Chem., 1992, 35, 2591–2600), RP-68651 (Proc. Natl. Acad. Sci USA, 1991, 88, 10208–10212), SR 140333 (Curt. J. Pharmacol., 1993, 250, 403–413).

For receptor $NK_2$, a selective non peptide antagonist, SR 48968, has been described in detail (Life Sci., 1992, 50, PL101–PL106).

Turning to receptor $NK_3$, some non peptide compounds have been described as having an affinity for receptor $NK_3$ in the rat and guinea pig-brain (FASEB J., 1993, 7(4), A710, 4104); a peptide antagonist [$Trp^7,\beta Ala^8$]$NK_A$, which is weakly specific for receptor $NK_3$ in the rat brain, has also been described (J. Autonomic Pharmacol., 1993, 13, 23–93).

European patent application EP-A-0 336 230 describes peptide derivatives which are antagonists of substance P and neurokinin A and are suitable for the treatment and prevention of asthma.

International patent applications WO 90/05525, WO 90/05729, WO 91/09844, WO 91/08899 and European patent applications EP-A-0 436 334, EP-A-0 429 466 and EP-A-0 430 771 describe antagonists of substance P.

European applications EP-A-0 474 561, EP-A-0 512 901, EP-A-0 515 240, EP-A-0 559 538 and EP-A-0 591 040 also concern antagonists of neurokinin receptors.

Novel salts of substituted nitrogenous hetero-aromatic compounds which are antagonists for neurokinins have now been discovered.

In one aspect, therefore, the present invention concerns compounds of formula:

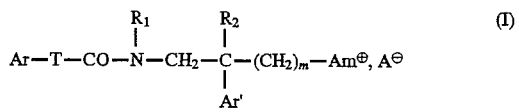

where:

Ar represents an aromatic or heteroaromatic mono-, di- or tricyclic group which may be substituted;

T represents a direct bond; a hydroxymethylene group; a $(C_1-C_4)$alkoxymethylene group; a $(C_1-C_5)$alkylene group; an oxygen atom; a —$NR_3$ group; vinylene;

Ar' represents phenyl which may be unsubstituted or phenyl substituted one or more times by a substituent selected from: a halogen atom, trifluoro-methyl, hydroxy, $(C_1-C_4)$alkoxy, $(C_1-C_4)$alkyl, said substituents being identical or different; thienyl; benzothienyl; naphthyl; indolyl which may be N-substituted by $(C_1-C_4)$alkyl or benzyl;

$R_1$ represents hydrogen; $(C_1-C_4)$alkyl; ω-hydroxy-$(C_2-C_4)$alkylene; ω-$(C_1-C_4)$alkoxy-$(C_2-C_4)$alkylene; ω-benzyloxy-$(C_2-C_4)$alkylene; ω-formyloxy-$(C_2-C_4)$alkylene; ω-$(C_1-C_4)$alkylcarbonyloxy-$(C_2-C_4)$alkylene; ω-benzoyloxy-$(C_2-C_4)$ alkylene; ω-$R_6$NHCOO—$(C_2-C_4)$alkylene; ω-$(C_1-C_4)$alkylthio-$(C_2-C_4)$alkylene; ω-carboxy-$(C_2-C_4)$alkylene; ω-$(C_1-C_4)$alkoxycarbonyl-$(C_2-C_4)$alkylene; ω-$R_7R_8$NCO—$(C_2-C_4)$alkylene; ω-$R_9R_{10}$N—$(C_2-C_4)$alkylene; ω-$R_{11}$CONR$_{12}$—$(C_2-C_4)$alkylene; ω-$R_{13}$OCONR$_{12}$—$(C_2-C_4)$alkylene; ω-$R_7R_8$NCONR$_{12}$—$(C_2-C_4)$alkylene; ω-$R_{14}SO_2NR_{12}$—$(C_2-C_4)$alkylene; ω-$(C_1-C_4)$alkylcarbonyl-$(C_2-C_4)$alkylene; ω-cyano-$(C_1-C_3)$alkylene;

$R_2$ represents hydrogen;

or $R_1$ and $R_2$ together form a 1,2-ethylene, 1,3-propylene or 1,4-butylene group;

$R_3$ represents hydrogen or $(C_1-C_4)$alkyl;

$Am^+$ represents a substituted 1-pyridylium radical of formula:

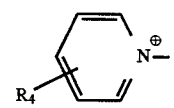

or a substituted 3-thiazolylium radical of formula:

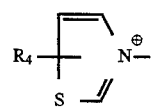

or a substituted 1-pyridazinylium radical of formula:

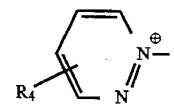

or a substituted 3-imidazolylium radical of formula:

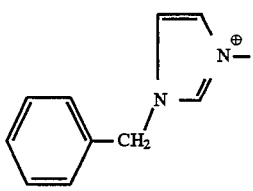

$R_4$ represents a group:

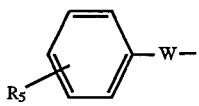

W represents a direct bond; a methylene group; an oxygen atom; a sulfur atom; a —$NR_3$— group;

$R_5$ represents hydrogen; a halogen; hydroxy; ($C_1$–$C_4$) alkoxy; ($C_1$–$C_4$)alkyl; trifluoromethyl;

$R_6$ represents ($C_1$–$C_7$)alkyl or phenyl;

$R_7$ and $R_8$ each independently represent hydrogen or ($C_1$–$C_7$)alkyl; $R_8$ may also represent ($C_3$–$C_7$) cycloalkyl, ($C_3$–$C_7$)cycloalkylmethyl, phenyl or benzyl;

or $R_7$ and $R_8$ together with the nitrogen atom to which they are bound constitute a heterocycle selected from azetidine, pyrrolidine, piperidine, morpholine, thiomorpholine or perhydroazepine;

$R_9$ and $R_{10}$ each independently represent hydrogen or a ($C_1$–$C_7$)alkyl; $R_{10}$ may also represent ($C_3$–$C_7$) cycloalkylmethyl or benzyl;

$R_{11}$ represents hydrogen, ($C_1$–$C_7$)alkyl, vinyl, phenyl, benzyl, pyridyl or ($C_3$–$C_7$)cycloalkyl which may be unsubstituted or substituted by one or more methyl groups;

$R_{12}$ represents hydrogen or ($C_1$–$C_7$)alkyl;

$R_{13}$ represents ($C_1$–$C_7$)alkyl or phenyl;

$R_{14}$ represents ($C_1$–$C_7$)alkyl; a free amino group or an amino group substituted by one or two ($C_1$–$C_7$)alkyls; phenyl which may be unsubstituted or substituted one or more times by a substituent selected from: a halogen atom, ($C_1$–$C_7$)alkyl, trifluoromethyl, hydroxy, ($C_1$–$C_7$) alkoxy, carboxy, ($C_1$–$C_7$)alkoxycarbonyl, ($C_1$–$C_7$) alkylcarbonyloxy, cyano, nitro, a free amino group or an amino group substituted by one or two ($C_1$–$C_7$) alkyls, said substituents being identical or different;

m is 2 or 3;

$A^-$ is an anion;

and their eventual salts with mineral or organic acids.

More particularly, radical Ar can be a phenyl group, which can be unsubstituted or may contain one or more substituents.

When Ar is a phenyl group, this can be mono- or disubstituted particularly in the 2,4 position, but also, for example, in the 2,3; 4,5; 3,4; or 3,5 position; it can also be trisubstituted, in particular in the 2,4,6 position but also, for example, in the 2,3,4; 2,3,5; 2,4,5; or 3,4,5 position; tetrasubstituted, for example in the 2,3,4,5 position; or pentasubstituted.

Radical Ar can also represent a bicyclic aromatic group such as 1- or 2-naphthyl; 1-, 2-, 3-, 4-, 5-, 6-, 7-indenyl, in which one or more bonds may be hydrogenated, these groups may be unsubstituted or may optionally contain one or more substituents such as: an alkyl, phenyl, cyano, hydroxyalkyl, hydroxy, oxo, alkylcarbonylamino, alkoxycarbonyl, thioalkyl, halogen, alkoxy, or trifluoromethyl group, where the alkyl groups are $C_1$–$C_4$.

Radical Ar may also be a pyridyl, thiadiazolyl, indolyl, indazolyl, imidazolyl, benzimidazolyl, benzo-triazolyl, benzofuranyl, benzothienyl, benzothiazolyl, benzisothiazolyl, quinolyl, isoquinolyl, benzoxazolyl, benzisoxazolyl, benzoxazinyl, benzodioxinyl, isoxazolyl, benzopyranyl, thiazolyl, thienyl, furyl, pyranyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromannyl, chromannyl, carboxyaryl, in which one or more double bonds may be hydrogenated, said groups being unsubstituted or may contain one or more substituents such as: alkyl, phenyl, cyano, hydroxyalkyl, hydroxy, alkylcarbonylamino, alkoxycarbonyl, thioalkyl, in which the alkyl groups are $C_1$–$C_4$.

In particular, the invention concerns compounds of formula (I) in which:

Ar represents:

phenyl which may be unsubstituted or substituted one or more times by a substituent selected from: a halogen atom; trifluoromethyl; cyano; hydroxy; nitro; amino which may be unsubstituted or amino substituted one or more times by ($C_1$–$C_4$)alkyl; benzyl-amino; carboxy; ($C_1$–$C_{10}$)alkyl; ($C_3$–$C_8$) cycloalkyl which may be unsubstituted or substituted one or more times by methyl; ($C_1$–$C_{10}$)alkoxy; ($C_3$–$C_8$)cycloalkyloxy which may be unsubstituted or substituted one or more times by methyl; mercapto; ($C_1$–$C_{10}$)alkylthio; formyloxy; ($C_1$–$C_6$)alkylcarbonyloxy; formylamino; ($C_1$–$C_6$) alkylcarbonylamino; benzoylamino; ($C_1$–$C_4$) alkoxycarbonyl; ($C_3$–$C_7$)cycloalkyloxycarbonyl; carbamoyl which may be unsubstituted or substituted one or more times by ($C_1$–$C_4$)alkyl; ureido which may be unsubstituted or substituted one or more times in the 3 position by ($C_1$–$C_4$)alkyl or ($C_3$–$C_7$)cycloalkyl; (pyrrolodine-1-yl) carbonylamino, the substituents being identical or different;

naphthyl which may be unsubstituted or substituted one or more times by a halogen, trifluoro-methyl, ($C_1$–$C_4$)alkyl, hydroxy, ($C_1$–$C_4$)alkoxy;

pyridyl; thienyl; indolyl; quinolyl; benzo-thienyl; imidazolyl.

Advantageously, the invention concerns compounds of formula (I) in which:

Ar represents:

phenyl which may be unsubstituted or substituted one or more times by a substituent selected from: a halogen atom; trifluoromethyl; cyano; hydroxy; nitro; amino which may be unsubstituted or substituted one or more times by ($C_1$–$C_4$)alkyl; benzylamino; carboxy; ($C_1$–$C_{10}$)alkyl; ($C_3$–$C_8$)cycloalkyl which may be unsubstituted or substituted one or more times by methyl; ($C_1$–$C_{10}$)alkoxy; ($C_3$–$C_8$) cycloalkyloxy which may be unsubstituted or substituted one or more times by methyl; mercapto; ($C_1$–$C_{10}$)alkylthio; ($C_1$–$C_6$)alkylcarbonyloxy; ($C_1$–$C_6$)alkylcarbonylamino; benzoylamino; ($C_1$–$C_4$)alkoxycarbonyl; ($C_3$–$C_7$) cycloalkyloxycarbonyl; carbamoyl which may be unsubstituted or substituted one or more times by ($C_1$–$C_4$)alkyl; ureido which may be unsubstituted or substituted one or more times in the 3 position by ($C_1$–$C_4$)alkyl or ($C_3$–$C_7$)cycloalkyl; (pyrrolidin-1-yl) carbonylamino, the substituents being identical or different;

naphthyl which may be unsubstituted or substituted one or more times by a halogen, trifluoro-methyl, $(C_1-C_4)$alkyl, hydroxy, $(C_1-C_4)$alkoxy;

pyridyl; thienyl; indolyl; quinolyl; benzo-thienyl; imidazolyl;

T represents a direct bond; a hydroxymethylene group; a $(C_1-C_4)$alkoxymethylene group; a $(C_1-C_5)$alkylene group; an oxygen atom; a $—NR_3$ group; vinylene;

Ar' represents phenyl which may be unsubstituted or substituted one or more times by a substituent selected from: a halogen atom, trifluoromethyl, hydroxy, $(C_1-C_4)$alkoxy, $(C_1-C_4)$alkyl, said substituents being identical or different; thienyl; benzothienyl; naphthyl; indolyl which may be N-substituted by a $(C_1-C_4)$alkyl or a benzyl group;

$R_1$ represents hydrogen; $(C_1-C_4)$alkyl; ω-hydroxy-$(C_2-C_4)$ alkylene; ω-$(C_1-C_4)$alkoxy-$(C_2-C_4)$alkylene; ω-$(C_1-C_4)$alkylcarbonyloxy$(C_2-C_4)$alkylene; ω-benzoyloxy-$(C_2-C_4)$ alkylene; ω-$(C_1-C_4)$alkylthio-$(C_2-C_4)$alkylene; ωcarboxy carboxy-$(C_2-C_4)$alkylene; ω-$(C_1-C_4)$alkoxycarbonyl-$(C_2-C_4)$ alkylene; ω-$(C_1-C_4)$alkylcarbonyl-$(C_2-C_4)$alkylene;

$R_2$ represents hydrogen;

or $R_1$ and $R_2$ together form a 1,2-ethylene, 1,3-propylene or 1,4-butylene group;

$R_3$ represents hydrogen or $(C_2-C_4)$alkyl;

$Am^+$ represents a substituted 1-pyridylium radical of formula:

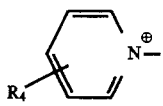

or substituted 3-thiazolylium radical of formula:

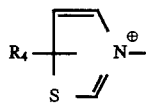

or a substituted 1-pyridazinylium radical of formula:

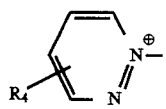

a substituted 3-imidazolylium radical of formula:

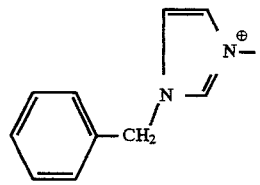

$R^4$ represents a group:

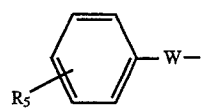

W represents a direct bond; a methylene group; an oxygen atom; a sulfur atom; a $—NR_3$—group;

$R_5$ represents hydrogen; a halogen; hydroxy; $(C_1-C_4)$ alkoxy; $(C_1-C_4)$alkyl; trifluoromethyl;

m is 2;

$A^-$ is an anion.

Compounds of formula (I) in accordance with the invention include both optically pure isomers and racemic mixtures.

Salts in addition to quaternary salts can be formed with the compounds of formula (I). These salts include those formed with mineral or organic acids which allow separation or crystallisation of compounds of formula (I) such as picric acid or oxalic acid or an optically active acid, for example mandelic or camphosulfonic acid, and those which form pharmaceutically acceptable salts such as the hydrochloride, hydrobromide, sulfate, hydrogensulfate, dihydrogenphosphate, methanesulfonate, methylsulfate, maleate, fumarate, 2-naphthalenesulfonate benzenesulfonate, glyconate, gluconate, citrate, isethionate, or para-toluenesulfonate.

The anions are those normally used to form salts of quaternary ammonium ions, preferably chloride, bromide, iodide, acetate, hydrogensulfate, methanesulfonate, para-toluenesulfonate and benzenesulfonate.

In the present description, the alkyl or alkoxy groups are straight chained or branched; the term halogen atom means a chlorine, bromine, fluorine or iodine atom.

Regarding the substituents for the phenyl group, the term $(C_1-C_{10})$alkyl means, for example, methyl, ethyl, n-propyl, isopropyl, n-butyl, isobutyl, sec-butyl, tert-butyl, pentyl or n-pentyl, hexyl or n-hexyl, heptyl or n-heptyl, octyl or n-octyl, nonyl or n-nonyl, decyl or n-decyl; the term $(C_3-C_8)$ cycloalkyl which may be substituted by methyl means, for example, cyclopropyl, cyclobutyl, cyclopentyl, 1-, 2- or 3-methylcyclopentyl, cyclohexyl, 1-, 2-, 3- or 4-methylcyclohexyl, cycloheptyl or cyclooctyl; the term $(C_1-C_{10})$ alkoxy means, for example, methoxy, ethoxy, n-propoxy, isopropoxy, n-butoxy, isobutoxy, sec-butoxy, tert-butoxy, pentyloxy, hexyloxy, heptyloxy, octyloxy, nonyloxy or decyloxy; the term $(C_3-C_8)$cycloalkyloxy which may be substituted by methyl means, for example, cyclopropyloxy, cyclobutyloxy, cyclopentyloxy, 1-, 2- or 3-methylcyclopentoxy, cyclohexyloxy, 1-, 2-, 3- or 4-methylcyclohexyloxy, cycloheptyloxy or cyclooctyloxy; the term $(C_1-C_{10})$alkylthio means, for example, methyl-thio, ethylthio, n-propylthio, isopropylthio, n-butyl-thio, isobutylthio, sec-butylthio, tert-butylthio, pentylthio, hexylthio, heptylthio, octylthio, nonylthio or decylthio; the term $(C_1-C_6)$alkylcarbonyloxy means, for example, acetyloxy, propionyloxy, butyryloxy, valeryloxy, caproyloxy, heptanoyloxy; the term $(C_1-C_6)$ alkylcarbonylamino means, for example, acetyl-amino, propionylamino, butyrylamino, isobutyrylamino valerylamino, caproylamino or heptanoylamino; the term $(C_1-C_4)$alkoxycarbonyl means, for example, methoxycarbonyl, ethoxycarbonyl, n-propoxycarbonyl, isopropoxycarbonyl, n-butoxycarbonyl, iso-butoxycarbonyl, sec-butoxycarbonyl or tert-butoxycarbonyl; the term $(C_3-C_7)$cycloalkyloxycarbonyl means, for example, cyclopropyloxycarbonyl, cyclobutyloxycarbonyl, cyclopentyloxycarbonyl, cyclohexyloxycarbonyl or cycloheptyloxycarbonyl.

Advantageously, radical Ar represents phenyl which may be unsubstituted or substituted one or more times by a halogen atom, more particularly a chlorine, fluorine or iodine atom, trifluoromethyl, $(C_1-C_4)$alkyl, hydroxy, $(C_1-C_4)$alkoxy; naphthyl which may be unsubstituted or substituted one or more times by a halogen, trifluoromethyl, $(C_1-C_4)$alkyl, hydroxy, $(C_1-C_4)$alkoxy; pyridyl; thienyl; indolyl; quinolyl; benzothienyl; imidazolyl. More particularly, radical Ar is a phenyl group substituted by an isopropoxy group, advantageously in the 3 position.

In formula (I), T preferably represents a methylene group.

Substituents $R_1$ and $R_2$ are preferably respectively a methyl group and hydrogen; a 2-methoxyethyl group and hydrogen; a 2-acetoxyethyl group and hydrogen; a 2-hydroxyethyl group and hydrogen; or $R_1$ and $R_2$ together form a 1,3-propylene group.

Substituent Ar' is preferably a phenyl group, advantageously substituted by two chlorine atoms or two fluorine atoms, more particularly in the 3 and 4 positions.

Substituent $Am^+$ in formula (I) is preferably the substituted 1-pyridylium radical:

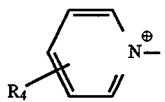

where $R_4$ is preferably an unsubstituted phenyl group or an unsubstituted benzyl group.

Particularly preferred compounds of the present invention are those with formula (I) in which, at the same time:

Ar is a 3-isopropoxyphenyl group;

T is a methylene group;

$R_1$ and $R_2$ are respectively a methyl group and hydrogen; a 2-acetoxyethyl group and hydrogen; a 2-hydroxyethyl group and hydrogen; or together form a 1,3-propylene group;

Ar' is 3,4-dichlorophenyl or 3,4-difluorophenyl;

$Am^+$ is a 1-pyridylium radical substituted in the 4 position by a phenyl or benzyl group;

m is 2;

$A^-$ is a pharmaceutically acceptable anion.

These substances, represented by formula:

in which iPr represents the isopropyl radical; Ar" represents 3,4-dichlorophenyl or 3,4-difluorophenyl; $R'_1$ and $R'_2$ respectively represent a methyl group and hydrogen, a 2-acetoxyethyl group and hydrogen; a 2-hydroxyethyl group and hydrogen; or together form a 1,3-propylene group; $R'_4$ is a phenyl or benzyl group, and $A^-$ is a pharmaceutically acceptable anion, are powerful antagonists for the substance P receptor.

Compounds with formula (I') in which $R'_1$ and $R'_2$ respectively represent a methyl group and hydrogen, or together form a 1,3-propylene group, have a strong affinity for the substance P receptor. They thus constitute the preferred aspect of the present invention.

Of these compounds, those of formulae (I") and (I'''):

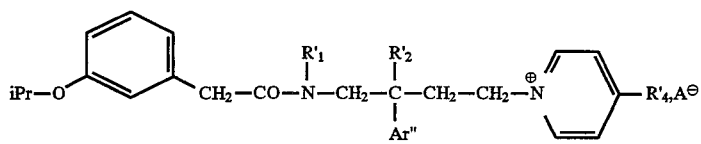
(I')

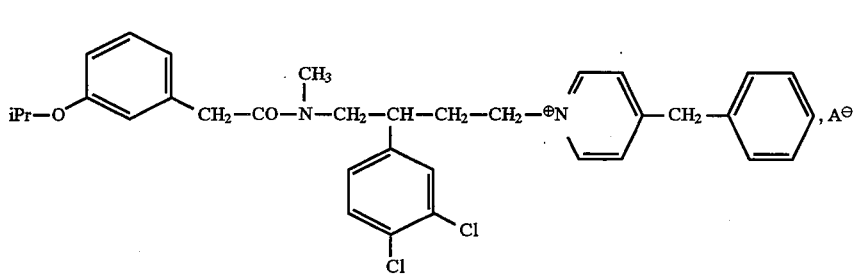
(I")

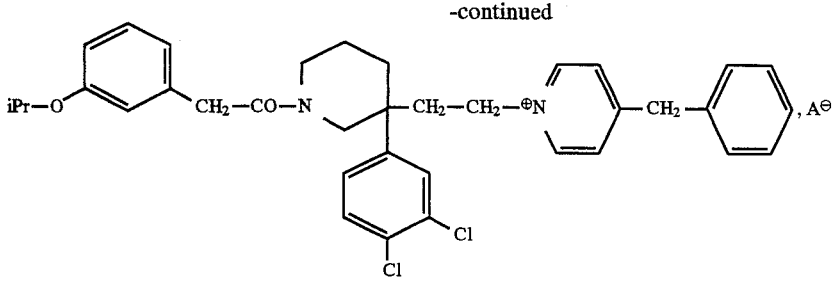
(I''')

where A⁻ is a pharmaceutically acceptable anion, are particularly preferred.

Pharmaceutically acceptable anions of compounds I', I'' and I''' are selected from chlorine, bromine, iodine, hydrogensulfate, methanesulfonate, paratoluenesulfonate, acetate and benzenesulfonate ions.

In a further aspect, the present invention concerns a process for the preparation of compounds of formula (I) above, characterized in that a derivative of the following formula:

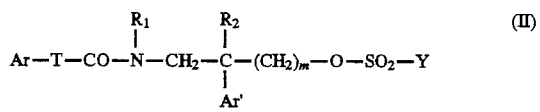
(II)

in which Y represents a methyl, phenyl, tolyl, or trifluoromethyl group and Ar, m, T, $R_1$, $R_2$ and Ar' are as defined above for (I), provided that when $R_1$ represents a ω-hydroxy-$(C_2-C_4)$alkylene group, the hydroxy group is protected, and when $R_1$ represents a ω-amino-$(C_2-C_4)$ alkylene group, the amino group is protected, is treated by an aromatic heterocycle with formula (III):

(III)

in which Am represents pyridine substituted by $R_4$, thiazole substituted by $R_4$, pyridazine substituted by $R_4$, or 1-benzylimidazole, and $R_4$ is as defined above for (I), in an organic solvent at a temperature between room temperature and 120° C. and, after any necessary deprotection of the hydroxy group or the amino group, the salt obtained is isolated in the form of a sulfonate, or the sulfonate anion ($YSO_3^-$) of the salt obtained is exchanged with another anion, and optically pure isomers are optionally separated.

The organic solvent is preferably a polar aprotic solvent, for example acetonitrile, N,N-dimethyl-formamide, or N,N-dimethylphenylacetamide. An ether, for example tetrahydrofuran, dioxane, or methyl-tert-butylether, or a ketone, for example methylethylketone, can also be used. Acetonitrile is particularly preferred.

Within the temperature range indicated above, the preferred temperature is 70°–90° C. When acetonitrile is used as the solvent, it is advantageous to reflux the reaction mixture.

The O-protecting groups used to obtain a compound with formula (I) in which $R_1$ represents ω-hydroxy-$(C_2-C_4)$ alkylene are conventional O-protecting groups which are known to the skilled person, such as acetyl or benzoyl, for example.

The N-protecting groups used to obtain a compound of formula (I) in which $R_1$ represents ω-amino-$(C_1-C_4)$ alkylene are conventional N-protecting groups which are known to the skilled person, such as tertbutoxycarbonyl, for example.

More particularly, when using an acetyl or benzoyl group as an O-protecting group, the compound of formula (I) obtained is the final product in which $R_1$ represents ω-acetoxy-$(C_1-C_4)$alkylene or ω-benzoyloxy-$(C_2-C_4)$ alkylene. The compounds of formula (I) thus obtained are hydrolysed using normal methods to obtain compounds of formula (I) in which $R_1$ represents ω-hydroxy-$(C_2-C_4)$ alkylene.

More particularly, when using a tert-butoxy-carbonyl group as an N-protecting group, the compound of formula (I) obtained is the final product in which $R_1$ represents ω-$R_{13}$OCONR$_{12}$—$(C_2-C_4)$alkylene in which $R_{13}$ represents the tert-butyl radical.

The product obtained is isolated using the normal techniques, for example by concentrating the solvents followed by washing the residue with diethyl ether followed by purification using conventional techniques, for example chromatography or recrystallization.

The sulfonate anion $YSO_3^-$ from the reaction between the aromatic heterocycle with formula (III) and the derivative with formula (II) can be exchanged, in situ or after isolation of compound (I) in which A⁻ is the $YSO_3^-$ ion, by another anion A⁻, using conventional methods, for example exchange in solution with a saturated solution of sodium chloride or with a solution of hydrochloric acid when A⁻ represents a chloride anion, or by exchanging the anion by eluting compound (I) on an ion exchange resin, for example Amberlite IRA68 or Duolite A375.

The derivatives of formula (II) used as starting compounds for the process of the present invention can be prepared by following SCHEME 1 below, which distinguishes:

ROUTE A: $R_2$=H; $R'_1$=H, $(C_1-C_4)$alkyl, ω-hydroxy-$(C_2-C_4)$alkylene, ω-$(C_1-C_4)$alkoxy-$(C_2-C_4)$alkylene, ω-$(C_1-C_4)$alkylthio-$(C_2-C_4)$alkylene, ω-$(C_1-C_4)$alkylcarbonyl-$(C_2-C_4)$alkylene, ω-carboxy-$(C_2-C_4)$alkylene, ω-$(C_1-C_4)$alkoxycarbonyl-$(C_2-C_4)$alkylene, ω-$R_7R_8$NCO—$(C_1-C_4)$ alkylene, ω-cyano-$(C_2-C_3)$ alkylene; $R_1$=$R'_1$, ω-benzyloxy-$(C_2-C_4)$alkylene, ω-formyloxy-$(C_2-C_4)$alkylene, ω-$(C_1-C_4)$alkylcarbonyloxy-$(C_2-C_4)$alkylene, ω-benzoyloxy-$(C_2-C_4)$ alkylene; ω-$R_6$NHCOO—$(C_2-C_4)$alkylene, ω-$R_9R_{10}$N—$(C_2-C_4)$ alkylene, ω-$R_{11}$CONR$_{12}$—$(C_2-C_4)$alkylene, ω$R_7R_8$NCONR$_{12}$—$C_2-C_4$ alkylene, ω-$R_{13}$CONR$_{12}$—$(C_1-C_4)$alkylene, ω$R_{14}SO_2NR_{12}$—$(C_2-C_4)$alkylene;

and ROUTE B: $R_1$+$R_2$=—$(CH_2)_n$-where n=2, 3, 4,

T represents, in the formulae indicated in SCHEME 1, a direct bond, a hydroxymethylene group, a $(C_1-C_4)$ alkoxymethylene group, a $(C_1-C_5)$alkylene group or a vinylene group;

$R'_3$ represents, in the formulae indicated in SCHEME 1, a $(C_1-C_4)$alkyl group.

SCHEME 1

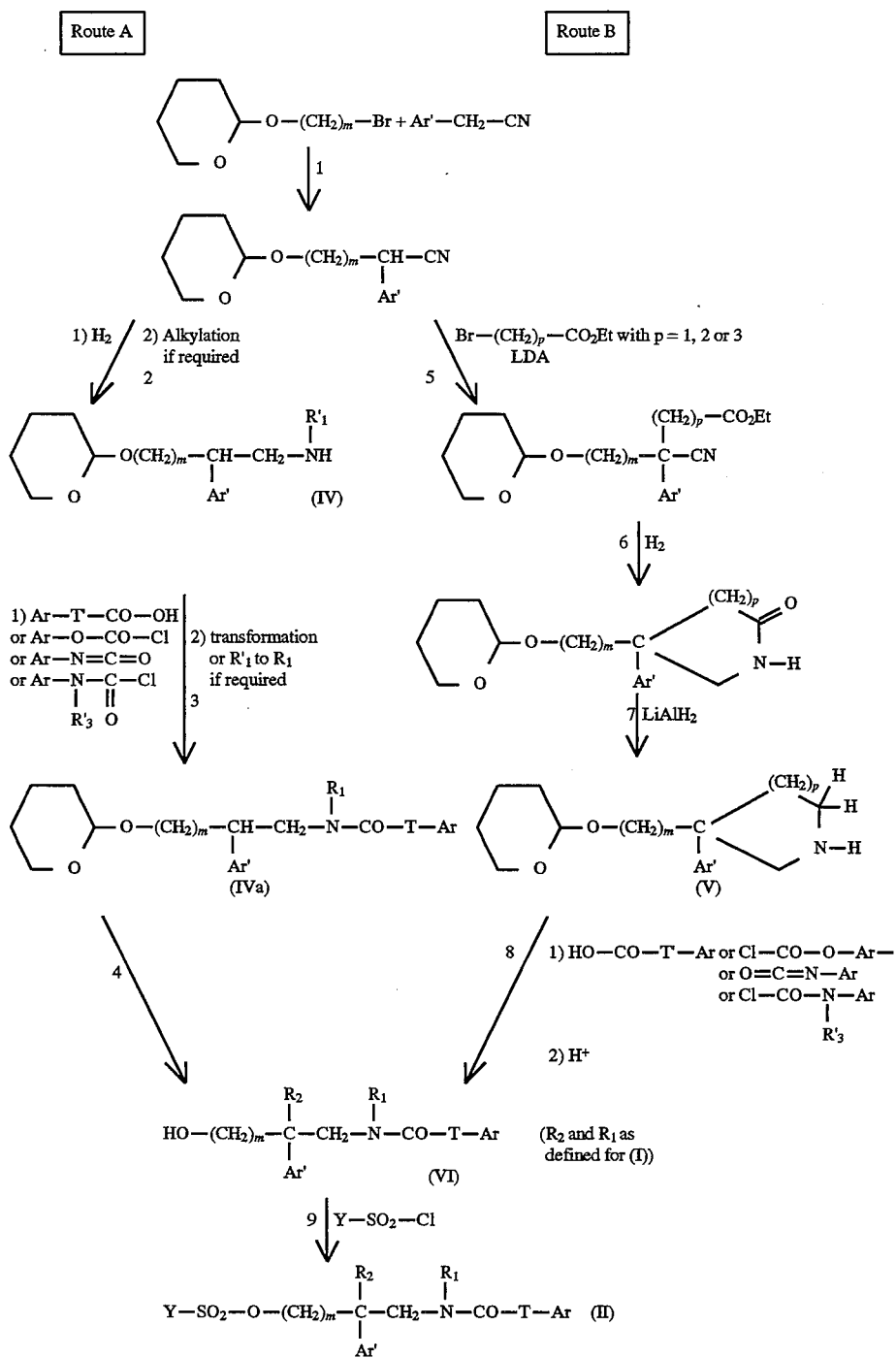

In SCHEME 1, the reactions in the different steps are shown representatively to indicate the reaction type; the means employed are known.

Step 1 in SCHEME 1 is described in European patent applications EP-A 0 428 434 and EP-A-0 474 561.

In Route A, step 2, and in Route B step 6, "$H_2$" means that the starting nitrile is reduced, for example by catalytic hydrogenation (Raney-Ni in ethanol in the presence of ammonia). In Route A, the primary amine (IV, $R'_1$=H) is obtained; in Route B, a lactam is obtained after in situ intramolecular cyclisation.

In the same step 2 in Route A, the term "alkylation" means that after reduction, the primary amine undergoes an alkylation reaction to introduce radical $R'_1$ other than H. When $R'_1$ is a $C_1$–$C_4$ alkyl, alkylation is carried out either directly by a halide or alkyl sulfate, or indirectly by acylation and reduction of the carbonyl group. Thus, for example, reaction of the primary amine (IV) with ethyl chloroformiate and reduction of the ethoxycarbonyl group produces the compound of formula (IV) where $R'_1$ is methyl, as described in EP-A-0 428 434 and EP-A-0 474 561. Ethyl chloroformiate can be replaced by di-tert-butyldicarbonate to prepare the compound of formula (IV) where $R'_1$ is methyl. Further, replacing ethyl chloroformiate with the chloride (or another functional derivative) of a $C_2$–$C_4$ alkanoic acid and reduction of the carbonyl group of the N-acylated derivative obtained produces the compound of formula (IV) in which $R'_1$ is $C_2$–$C_4$ alkyl.

In order to obtain compounds of formula (IV) in which $R'_1$ is ω-hydroxy-($C_2$–$C_4$)alkylene, a compound of formula (IV) in which $R'_1$=H is treated with ethyl-oxalyl chloride, ethyl hemimalonate or ethyl hemisuccinate, for example, to obtain the corresponding N-acylated derivatives. The carbonyl groups are then reduced using known methods such as the action of a reducing agent, for example a metallic hydride such as lithium aluminium hydride or a boron hydride, such as borane dimethylsulfide. Reduction is carried out in a solvent such as tetrahydrofuran or toluene at a temperature in the range of 0° C. to 70° C. In particular, glycolic acid can be reacted with a compound of formula (IV) in which $R'_1$=H in the presence of benzotriazol-1-yloxytris(dimethylamino) phosphonium hexafluorophosphate and triethylamine to obtain the corresponding N-acylated derivative which, after reduction of the carbonyl group, produces a compound with formula (IV) in which $R'_1$ represents a 2-hydroxyethyl group.

To prepare a compound of formula (IV) in which $R'_1$ represents ω-($C_1$–$C_4$)alkoxy-($C_2$–$C_4$)alkylene, a compound of formula (IV) in which $R'_1$=H is reacted with an ω-($C_1$–$C_4$)alkoxy-($C_2$–$C_4$)alkanoic acid using conventional peptide coupling methods, then the carbonyl group of the N-acylated derivative obtained as an intermediate is reduced.

To prepare a compound of formula (IV) in which $R'_1$ represents ω-($C_1$–$C_4$)alkylthio-($C_2$–$C_4$)alkylene, a compound of formula (IV) in which $R'_1$=H is reacted with an ω-halogeno-($C_2$–$C_4$)alkylenethioalkyl-($C_1$–$C_4$) such as 2-chloro-1-(methylthio)ethane using conventional alkylation methods.

To prepare a compound of formula (IV) in which $R'_1$ represents ω-($C_1$–$C_4$)alkylcarbonyl-($C_2$–$C_4$)alkylene, a compound of formula (IV) in which $R'_1$=H is reacted with an ω-halogeno($C_2$–$C_4$)alkylenecarbonyl-($C_1$–$C_4$)alkyl such as 4-chlorobutan-2-one using conventional alkylation methods.

To prepare a compound of formula (IV) in which $R'_1$ represents ω-($C_1$–$C_4$)alkoxycarbonyl-($C_2$–$C_4$)alkylene, a compound of formula (IV) in which $R'_1$=H is reacted with a ($C_1$–$C_4$)alkyl ω-halogeno($C_2$–$C_4$)alkylenecarboxylate such as ethyl 3-bromopropionate, ethyl 4-bromobutyrate or ethyl 5-bromovalerate using conventional alkylation methods.

Conventional hydrolysis of compounds with formula (IV) in which $R'_1$ represents a ω-($C_1$–$C_4$)alkoxycarbonyl-($C_1$–$C_4$) alkylene produces compounds of formula (IV) in which $R'_1$ represents ω-carboxy-($C_1$–$C_4$)alkylene.

Reaction of a compound of formula (IV) in which $R'_1$ represents ω-carboxy-($C_2$–$C_4$)alkylene with a compound of formula $NHR_7R_8$ using conventional peptide coupling methods produces a compound of formula (IV) in which $R'_1$ represents ω-$R_7R_8$NCO—($C_2$–$C_4$)alkylene.

To prepare a compound of formula (IV) in which $R'_1$ represents ω-cyano-($C_1$–$C_3$)alkylene, a compound of formula (IV) in which $R'_1$=H is reacted with chloroacetonitrile, 3-chloropropionitrile or 4-chlorobutyronitrile using conventional alkylation methods.

In step 3 of Route A, compound (IV) can be coupled with an acid with formula Ar—T—COOH using conventional peptide synthesis methods, when T represents a direct bond, a hydroxymethylene group, a ($C_1$–$C_4$)alkoxymethylene group, a $C_1$–$C_5$ alkylene group, or a vinylene group. Functional derivatives of this acid which react with amines can also be used, for example an anhydride, a mixed anhydride, an acid chloride or an activated ester such as the para-nitrophenyl ester.

When using the acid with formula Ar—T—COOH, the reaction is carried out in the presence of a coupling agent used in peptide chemistry such as 1,3-dicyclohexylcarbodiimide or benzotriazol-1-yloxytris(dimethylamino)phosphonium hexafluorophosphate in the presence of a base such as triethylamine or N,N-diisopropyl-ethylamine, in an inert solvent such as dichloromethane or N,N-dimethylformamide at a temperature of between 0° C. and room temperature.

When using an acid chloride, the reaction is carried out in an inert solvent such as dichloromethane or benzene, in the presence of a base such as triethyl-amine or N-methylmorpholine at a temperature of between −70° C. and room temperature.

When T represents an oxygen atom, the compound of formula (IV) is reacted with a chloroformiate with formula Ar—O—CO—Cl in a solvent such as dichloromethane at a temperature of between 0° C. and room temperature, in the presence of a base such as triethylamine.

When T represents a —$NR_3$— group in which $R_3$ represents hydrogen, the compound of formula (IV) is reacted with an isocyanate with formula Ar—N=C=O in an inert solvent such as dichloromethane or benzene at a temperature of between −70° C. and room temperature.

When T represents a —$NR_3$— group in which $R_3$ represents a $C_1$–$C_4$ alkyl, the compound of formula (IV) is reacted with a carbamoyl chloride with formula Ar—$NR'_3$—CO—Cl in which $R'_3$ represents $C_1$–$C_4$ alkyl, in a solvent such as toluene or 1,2-dichloroethane at a temperature in the range of 80° C. to 110° C. and in the presence of a base such as triethylamine.

Then in the same step 3 of Route A, if necessary the compound obtained undergoes subsequent treatment to prepare a compound of formula (IVa) by transforming group $R'_1$ to $R_1$, provided that when T represents a hydroxymethylene group, the hydroxy group is protected.

Thus when $R'_1$ represents ω-hydroxy-($C_2$–$C_4$)alkylene, then the hydroxy group may be protected if necessary or an O-acylation reaction can be carried out using known methods to obtain a compound of formula (IVa) in which $R_1$ represents ω-($C_1$–$C_4$)alkylcarbonyloxy-($C_2$–$C_4$)alkylene or ω-benzoyloxy-($C_2$–$C_4$)alkylene.

Reacting a compound in which $R'_1$ represents ω-hydroxy-($C_2$–$C_4$)alkylene with formic acid in acetic anhydride produces a compound of formula (IVa) in which $R_1$ represents ω-formyloxy-($C_2$–$C_4$)alkylene.

Reacting a compound in which $R'_1$ represents ω-hydroxy-($C_2$–$C_4$)alkylene with a benzyl halide using conventional methods produces a compound of formula (IVa) in which $R_1$ represents ω-benzyloxy-($C_2$–$C_4$)alkylene.

Reacting a compound in which $R'_1$ represents ω-hydroxy-($C_2$–$C_4$)alkylene with an isocyanate of formula $R_6$—N=C=O produces a compound of formula (IVa) in which $R_1$ represents ω-$R_6$NHCOO—($C_2$–$C_4$)alkylene.

A compound of formula (IVa) in which $R_1$ represents ω-$R_9R_{10}$N—($C_2$–$C_4$)alkylene where $R_9$=$R_{10}$=H is prepared from a compound in which $R'_1$ represents ω-hydroxy-($C_1$–$C_4$) alkylene using the method described in J. Med. Chem., 1989, 32, 391–396.

A compound of formula (IVa) in which $R_1$ represents ω-$R_9R_{10}$N—($C_2$–$C_4$)alkylene where $R_9$=$R_{10}$=H can also be prepared from a compound in which $R'_1$ represents ω-cyano-($C_1$–$C_3$)alkylene by reduction of the nitrile group, using methods known to the skilled person.

A compound of formula (IVa) in which $R_1$ represents $\omega\text{-}R_9R_{10}N\text{—}(C_2\text{-}C_4)$alkylene can also be prepared using the different steps in the process described in SCHEME 2.

SCHEME 2

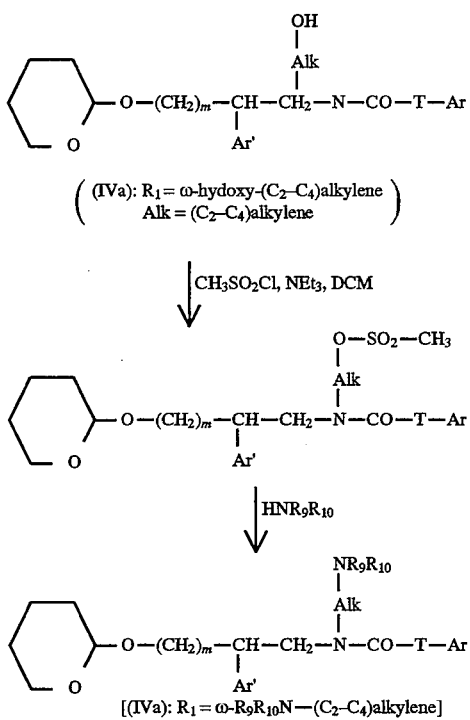

((IVa): $R_1 = \omega$-hydoxy-$(C_2\text{-}C_4)$alkylene
Alk = $(C_2\text{-}C_4)$alkylene)

[(IVa): $R_1 = \omega\text{-}R_9R_{10}N\text{—}(C_2\text{-}C_4)$alkylene]

To prepare a compound of formula (IVa) in which $R_1$ represents $\omega\text{-}R_{11}CONR_{12}\text{—}(C_2\text{-}C_4)$alkylene in which $R_{12}$ represents hydrogen or $(C_1\text{-}C_7)$alkyl and $R_{11}$ represents hydrogen or respectively $(C_1\text{-}C_7)$alkyl, vinyl, phenyl, benzyl, pyridyl or a $(C_3\text{-}C_7)$cycloalkyl which may be substituted, formic acid is reacted in acetic anhydride or respectively an appropriate anhydride of formula $(R_{11}CO)_2$ or an appropriate acid chloride of formula $R_{11}COCl$ in the presence of a base such as triethylamine, with a compound of formula (IVa) in which $R_1$ represents $\omega\text{-}HNR_{12}\text{—}(C_2\text{-}C_4)$ alkylene.

Similarly, compounds of formula (IVa) in which $R_1$ represents a $\omega\text{-}R_{13}OCONR_{12}\text{—}(C_2\text{-}C_4)$alkylene are prepared by the action of a chloroformiate of formula $R_{13}OCOCl$.

Compounds of formula (IVa) in which $R_1$ represents a $\omega\text{-}R_7R_8NOCONR_{12}\text{—}(C_2\text{-}C_4)$alkylene in which $R_7$ represents hydrogen are prepared by the action of an isocyanate of formula $R_8N=C=O$.

Compounds of formula (IVa) in which $R_1$ represents a $\omega\text{-}R_7R_8NCONR_{12}\text{—}(C_2\text{-}C_4)$alkylene in which $R_7$ represents a $(C_1\text{-}C_7)$alkyl are prepared by the action of a carbamoyl chloride of formula $R_7R_8NCOCl$.

Compounds of formula (IVa) in which $R_1$ represents a $\omega\text{-}R_{14}SO_2NR_{12}\text{—}(C_2\text{-}C_4)$alkylene are prepared by the action of a sulfonyl chloride of formula $R_{14}SO_2Cl$.

In step 4 of Route A, the tetrahydropyran-2-yl group is eliminated from the compound of formula (IVa) using methods known to the skilled person, in particular acid hydrolysis.

Route B of SCHEME 1 uses a series of well-known reactions such as α-alkylation of a nitrile by a bromine-containing derivative in the presence of lithium diisopropylamide (LDA) (step 5), followed by reduction of the nitrile by hydrogenation in the presence of a catalyst to obtain compound (V), in accordance with, for example, A. V. El'tsov et al, Biol. Aktivn. Soedin. Akad. Nauk. SSSR, 1965, 109–112 or using the processes described in EP-A-0 474 561.

In step 8 of Route B, the compound of formula (V) is reacted with an acid of formula Ar—T—COOH, a chloroformiate of formula Ar—OCOCl, an isocyanate of formula Ar—N=C=O or a carbamoyl chloride of formula Ar—N($R'_3$)—COCl using the methods described above.

Then in the same step 8 of Route B, the tetrahydropyran-2-yl group is eliminated from the compound obtained using known methods, in particular acid hydrolysis.

Derivative (II) is prepared by reacting the alcohol (VI) with a Y—SO_2—Cl derivative, for example methanesulfonyl chloride or benzenesulfonyl chloride (step 9) provided that when in the compound of formula (VI), $R_1$ represents $\omega$-hydroxy-$(C_2\text{-}C_4)$alkylene, the hydroxy group is protected and when $R_1$ represents $\omega$-amino-$(C_2\text{-}C_4)$alkylene, the amino group is protected.

Nitrogenous aromatic heterocycles of formula (III) are known or prepared using known methods.

Resolution of racemic mixtures (I) isolates enantiomers (I*) which also form part of the invention.

It is, however, preferable to separate the racemic mixtures using aminoalcohol intermediates of formula:

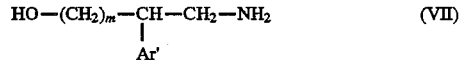 (VII)

and

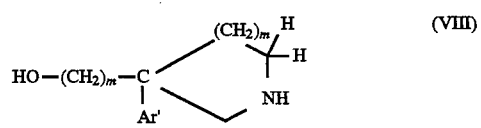 (VIII)

which can produce salts with optically active acids.

Aminoalcohols (VII) and (VIII) are obtained from compounds (IV, $R'_1$=H) and (V) in SCHEME 1 after deprotection by acid hydrolysis.

Enantiomers (VII*) and (VIII*) are then separated using conventional methods such as those described in EP-A-0 428 434, EP-A-0 474 561 and EP-A-0 512 901.

The preparation of optically pure compounds of formula (VI*) is illustrated in SCHEME 3 below, in which "*" means that the carbon atom thus labelled has the configuration (+) or (−).

SCHEME 3

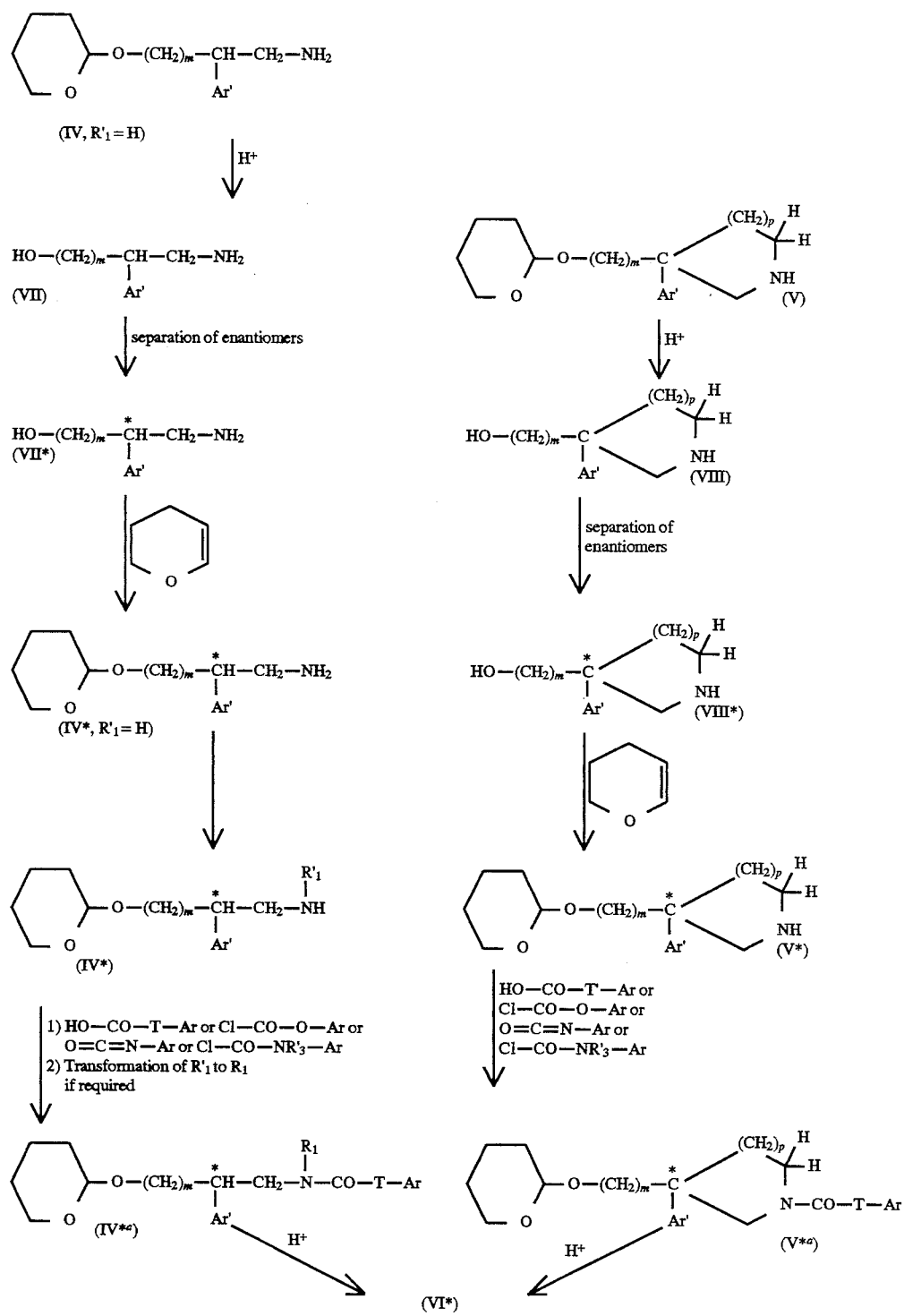

Thus compound (VII*) obtained after separation of the enantiomers of (VII) and after a step for protecting the hydroxy function, for example by reaction with 3,4-dihydro-2H-pyrane, undergoes substitution of the amine function to introduce the R'₁ group using the methods described to prepare compounds of formula (IV). Compound (IV*) obtained is thus reacted with an acid of formula Ar—T—COOH (or one of its functional derivatives) or with a chloroformiate of formula Ar—O—CO—Cl, with an isocyanate of formula Ar—N=C=O or with a carbamoyl chloride of formula Ar—NR'₃—CO—Cl using the methods described above. Then, if required, the compound obtained undergoes a subsequent treatment to prepare a compound of formula (IV*a) by transformation of the R'₁ group to R₁ using the methods described above.

In the same way, compound (VIII*) obtained after separation of the enantiomers of (VIII) and after any step required for protecting the hydroxy function, for example with 3,4-dihydro-2H-pyrane, is reacted with an acid with formula Ar—T—COOH (or one of its functional derivatives), with a chloroformiate of formula Ar—O—CO—Cl, with an isocyanate of formula Ar—N=C=O or with a carbamoyl chloride of formula Ar—NR′₃—CO—Cl using the methods described above. The compound obtained, of formula:

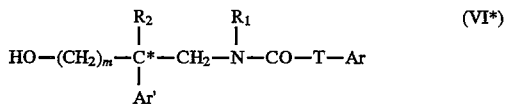

is then reacted with a Y-SO₂-Cl derivative in accordance with step 9 of SCHEME 1 to produce the optically pure derivative (II*) of formula:

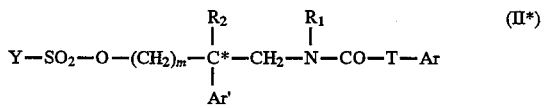

Compounds of formula (I) in which T represents a hydroxymethylene or $C_1$-$C_4$ alkoxymethylene group, have two centers of asymmetry. In this case, pure diastereoisomer and isomers can be prepared by reacting the optically pure (VII*) or (VIII*) aminoalcohol with either optically pure or racemic HO—CO—T—Ar acid in which T represents a hydroxymethylene group or a $C_1$-$C_4$ alkoxymethylene group. In the latter case, the diastereoisomer can be separated, for example by chromatography.

Reaction with the compound of formula (II) can produce compound (I*) of the invention in its optically pure form.

The above compounds of formula (I) also include those in which one or more hydrogen atoms or carbon atoms have been replaced by a radioactive isotope, for example tritium, carbon-14 or iodine-125. These labelled compounds are useful for research work (metabolic or pharmacokinetic) in biochemical tests as receptor ligands.

The affinity of compounds for tachykinin receptors has been evaluated in vitro by a number of biochemical tests using radioligands:

1) Bonding of [$^{125}$I]BH-SP (substance P labelled with iodine-125 using a Bolton-Hunter reagent) to $NK_1$ receptors in the rat cortex, the guinea pig ileum and human lymphoblastic cells.
2) Bonding of [$^{125}$I]His-NKa to $NK_2$ receptors in the rat duodenum or rat bladder.
3) Bonding of [$^{125}$I]His[MePHe$^7$]$NK_B$ to $NK_3$ receptors in the rat cerebral cortex, the guinea-pig cerebral cortex and the gerbil cerebral cortex and to cloned human $NK_3$ receptors expressed in CHO cells (Buell et al., FEBS Letters, 1992, 299, 90–95).

The tests were carried out as described in X. Emonds et al., (Eur. J. Pharmacol., 1993, 250, 403–413).

The compounds of the invention have an affinity for the tachykinin receptors cited above, with an inhibition index $K_i$ of less than $10^{-8}$M.

Of the compounds tested, 4-benzyl-1-[3,4-dichlorophenyl)-4-[N-methyl (3-isopropoxyphenyl)acetyl- amino] butyl]pyridinium methanesulfonate dihydrate and 4-benzyl-1-[2-[3-(3,4-dichlorophenyl)-1-[(3-isopropoxy-phenyl)acetyl]piperidin-3-yl]ethyl]pyridintum chloride dihydrate have been shown to be powerful antagonists of substance P receptor $NK_1$: they inhibit fixation of substance P to its receptor with an inhibition index ($K_i$) of between 0.2 and 0.5 nM in the various biochemical tests carried out.

The compounds of the present invention form the active ingredients in pharmaceutical compositions in which their toxicity is compatible with their use as medication.

Compounds with formula (I) above can be used in daily doses of 0.01 to 100 mg per kilo of body weight of the mammal to be treated, preferably in daily doses of 0.1 to 50 mg/kg. In humans, the dose is preferably 0.5 mg to 4000 mg per day, more particularly 2.5 mg to 1000 mg per day depending on the age of the person to be treated or the type of treatment: prophylactic or curative.

For use as medication, compounds with formula (I) are generally administered in unit doses. These unit doses are preferably formulated into pharmaceutical compositions in which the active ingredient is mixed with a pharmaceutical excipient.

Thus, in a further aspect, the present invention concerns pharmaceutical compositions containing a compound with formula (I) as an active ingredient.

In pharmaceutical compositions of the present invention for administration by the following routes: oral, sublingual, inhalation, sub-cutaneous, intramuscular, intravenous, transdermal, local or rectal, the active ingredients can be administered to animals or humans as administration units, mixed with normal pharmaceutical supports. Suitable administration units include forms for administration by the oral route such as tablets, capsules, powders, granules and oral solutions or suspensions, sublingual and buccal administration forms, aerosols, implants, subcutaneous, intramuscular, intravenous, intranasal or intraocular administration forms, and rectal administration forms.

When preparing a solid composition in the form of tablets, the principal active ingredient is mixed with a pharmaceutical vehicle such as silica, gelatine, starch, lactose, magnesium stearate, talc, gum arabic or analogous substances. The tablets can be coated with saccharose, various polymers or other suitable materials, or they may be treated so as to have a prolonged or delayed activity and so as to release a predetermined quantity of active ingredient continuously.

Capsules are prepared by mixing the active ingredient with a diluent such as a glycol or a glycerol ester and incorporating the mixture obtained into soft or hard capsules.

A preparation in the form of a syrup or elixir may contain the active ingredient with a sweetener, preferably caloriefree, methylparaben and propylparaben as an antiseptic, a flavoring agent and suitable coloring.

Powders or granules which can be dispersed in water may contain the active ingredient mixed with dispersing agents or softening agents, or suspension agents such as polyvinylpyrrolidone, also with sweeteners or taste correctors.

For rectal administration, suppositories are prepared using binders which melt at the rectal temperature, for example cocoa butter or polyethyleneglycols.

For parenteral, intranasal or intraocular administration, aqueous suspensions, isotonic saline solutions or sterile injectable solutions are used which contain dispersing agents and/or pharmacologically acceptable wetting agents, for example propyleneglycol or butyleneglycol.

For administration by inhalation, an aerosol used which contains, for example, sorbitane trioleate or oleic acid along with trichlorofluoromethane, dichlorofluoromethane dichlorotetrafluoromethans or any other biologically acceptable propellant; a system in the form of a powder comprising the active ingredient alone or combined with an excipient can also be used.

The active ingredient can also be formulated as microcapsules, which may contain one or more supports or additives.

In each unit dose, the active ingredient with formula (I) is present in a quantity suitable for the envisaged daily dose. In general, each unit dose is adjusted depending on the type of administration, for example tablets, capsules or the like, sachets, ampoules, syrups and the like, or drops such that each unit dose contains 0.5 to 1000 mg of active ingredient, preferably 2.5 to 250 mg, for administration one to four times a day.

In a further aspect, the present invention concerns the use of substances of formula (I) in preparing drugs for the treatment of physiological problems associated with an excess of tachykinins, in particular substance P and all tachykinin-dependent pathologies of the respiratory, gastro-intestinal, urinary, immune, cardiovascular and central nervous systems, as well as pain and migraine.

Non limiting examples are:

acute and chronic pain, linked for example to migraine, to the pain associated with cancer and angina, to chronic inflammatory processes such as osteoarthritis and rheumatoid arthritis;

inflammations such as chronic obstructive respiratory disease, asthma, allergies, rhinitis, coughs, bronchitis, hypersensitivity, for example to pollens and Acarida, rheumatoid arthritis, osteoarthritis, psoriasis, ulcerative colitis, Crohn's disease, irritable colon syndrome, prostatitis, neurological bladder, cystitis, urethritis, nephritis;

diseases of the immune system linked with suppression or stimulation of the function of immune cells, for example rheumatoid arthritis, psoriasis, Crohn's disease, diabetes, lupus, neuropsychiatric or neurological diseases of the central nervous system such as anxiety, depression psychosis, schizophrenia, mania, dementia, epilepsy, Parkinson's disease, Alzheimer's disease, drug dependence, Down's syndrome and Huntington's chorea, along with neurodegenerative diseases;

diseases of the gastro-intestinal system such as nausea, irritable colon syndrome, gastric and duodenal ulcers, diarrhoea, hypersecretion;

diseases of the cardiovascular system such as the vascular aspects of migraine, oedema, thrombosis, angina pectoris, vascular spasms and hypertension.

The present invention also includes a method of treating these afflictions with the doses indicated above.

In the preparations and examples, the following abbreviations have been used:

EtOH : ethanol
MeOH : methanol
Ether : diethyl ether
Ether iso: diisopropyl ether
DMF : dimethylformamide
EtOAc : ethyl acetate
DCM : dichloromethane
THF : tetrahydrofuran
NaOH : sodium hydroxide
iPr : isopropyl
RT : room temperature
MP : melting point
NMR : nuclear magnetic resonance
s : singlet
sd : doubled singlet
d : doublet
sept : septuplet
m : unresolved signal
mult : multiplet

PREPARATIONS

Preparation 1

(3-isopropoxyphenyl)acetic acid a) Ethyl ester of (3-hydroxyphenyl)acetic acid

A mixture of 55 g of (3-hydroxyphenyl)acetic acid in 400 ml of absolute EtOH and several drops of concentrated sulfuric acid was refluxed overnight. The reaction mixture was vacuum evaporated, the residue was taken up in ether, washed with water, then with a saturated solution of sodium hydrogencarbonate, dried over magnesium sulfate and the solvent was then vacuum evaporated. 58 g of the expected product was obtained as an oil which was directly used in the following step without purification.

b) Ethyl ester of (3-isopropoxyphenyl)acetic acid

A mixture of 58 g of the compound obtained in the previous step was heated for 8 hours at 80°–100° C. with 88 g of potassium carbonate and 108 g of 2-iodopropane in 300 ml of DMF. The reaction mixture was vacuum evaporated, the residue was taken up in EtOAc, washed with a 10% solution of potassium carbonate, dried over magnesium sulfate and the solvent was then vacuum evaporated. The residue was chromatographed on silica, eluting with DCM. 61 g of the expected product was obtained as an oil which was used as such in the following step.

c) (3-isopropoxyphenyl)acetic acid

A mixture of 31 g of the compound obtained from the preceding step, 20 g of NaOH and 400 ml of EtOH was refluxed for 2 hours. The reaction mixture was vacuum evaporated, the residue was taken up in water, acidified by adding concentrated hydrochloric acid to a pH of 1, extracted with ether, washed with water, dried over magnesium sulfate and the solvent was then vacuum evaporated. 27 g of the expected product was obtained. MP=33°–35° C.

Preparation 2

N-[2-(3,4-dichlorophenyl)-4-(methanesulfonyloxy)butl]-N-methyl(3-isopropoxyphenyl)acetamide.

a) 2-(3,4-dichlorophenyl)-4-(tetrahydropyran-2-yl-oxy) butanenitrile

A solution of 100 g of 3,4-dichlorophenylacetonitrile in 500 ml of THF was added dropwise over 30 minutes to a suspension of 16.5 g of sodium hydride in 200 ml of dry THF at 20° C. The reaction mixture was stirred for 2 hours at RT. It was then cooled to −20° C., and a solution of 118 g of 1-bromo-2-(tetrahydropyran-2-yloxy) ethane in 100 ml of THF was added and the mixture was stirred for 2 hours, allowing the temperature to increase back up to RT. A solution of 50 g of ammonium chloride in 3 liters of water was added, then the mixture was extracted with 1.5 liters of ether, washed with a saturated sodium chloride solution, dried over magnesium sulfate and vacuum evaporated. The residue was chromatographed on silica, eluting with DCM then a DCM/EtOAc (95/5; v/v) mixture. 118 g of the expected product was obtained as an oil which was used as such in the following step.

b) 2-(3,4-dichlorophenyl)-4-(tetrahydropyran-2-yl-oxy) butylamine.

300 ml of concentrated ammonia was added to a solution of 118 g of the nitrile obtained above in 700 ml of absolute ethanol in a nitrogen atmosphere. Raney nickel (10% of the starting quantity of the nitrile) was introduced. Hydrogenation was carried out at RT with a water pressure head. The catalyst was filtered through Celite then the filtrate was vacuum evaporated. The residue was taken up in a saturated sodium chloride solution, extracted with ether, dried over magnesium sulfate and the solvent was then vacuum evaporated. 112 g of the expected product was obtained as an oil which was used as such in the following step.

c) 2-(3,4-dichlorophenyl)-4-hydroxybutylamine.

80 ml of a saturated hydrochloric acid in ether was added to a solution of 81 g of the compound obtained from the preceding step in 38 ml of MeOH. The temperature was maintained at between 20° C. and 25° C. The reaction mixture was stirred for 30 minutes at RT then vacuum evaporated. The residue was dissolved in 250 ml of water, washed twice with ether, the aqueous phase was alkalinised by adding a 1N solution of NaOH, extracted with DCM, dried over magnesium sulfate and the solvent was vacuum evaporated. The residue was taken up in 800 ml of iso ether, the insoluble products were filtered out through Celite and the filtrate was vacuum concentrated to about 300 ml. The solution was seeded with crystals of the expected aminoalcohol, stirred overnight, the precipitated formed was filtered and washed with iso ether then with n-pentane. 30.2 g of the expected product was obtained. MP=90°–91° C.

d) N-tert-butoxy-2-(3,4-dichlorophenyl)-4-hydroxybutylamine

A solution of 48.96 g of di-tert-butyldicarbonate in 100 ml of EtOAc was added dropwise to a suspension of 50 g of the compound obtained in the preceding step in 250 ml of EtOAc and refluxed for 30 minutes. The reaction medium was washed twice with a buffer solution with pH=2, with water, then with a saturated sodium chloride solution, dried over magnesium sulfate and the solvent was vacuum evaporated. 72.79 g of the expected product was obtained as an oil which crystallized in hexane.

e) N-methyl-2-(3,4-dichlorophenyl)-4-hydroxybutylamine hydrochloride

A solution of 21.99 g of the compound obtained in the preceding step in 150 ml of THF was added dropwise to a suspension of 10 g of lithium aluminium hydride in 150 ml of anhydrous THF and refluxed for 7 hours. The reaction mixture was diluted with 300 ml of THF and 10 ml of water was slowly added, then 10 ml of a 4N solution of NaOH, then 30 ml of water and then stirred for 1 hour. The inorganic salts were filtered out through Celite, the filtrate was decanted and the organic phase was vacuum evaporated. The residue was taken up in acetone, a saturated solution of hydrochloric acid in ether was added until the pH was 1, stirred for 1 hour, and the crystals which formed were filtered out. The crystals were washed with acetone then with ether. 13.49 g of the expected product was obtained. MP=149° C.

f) N-methyl-2-(3,4-dichlorophenyl)-4-(tetrahydropyran-2-yloxy)butylamine hydrochloride A mixture of 13.04 g of the compound obtained from the preceding step, 5.78 g of 3,4-dihydro-2H-pyrane in 200 ml of DCM and several drops of a saturated solution of hydrochloric acid in ether was refluxed for 2 hours. After cooling, the reaction mixture was vacuum evaporated and the residue was recrystallized from hot acetone. 10.66 g of the expected product was obtained which was used as such in the following step.

g) N-[2-(3,4-dichlorophenyl)-4-(tetrahydropyran-2-yloxy)butyl]-N-methyl(3-isopropoxyphenyl)acetamide 8.78 g of triethylamine then 5.62 g of 3-isopropoxyphenylacetic acid and 14.11 g of BOP was added to a solution of 10.66 g of the compound obtained from the preceding step in 100 ml of DCM. The reaction mixture was stirred for 4 hours at RT then vacuum concentrated. The residue was extracted with EtOAc, washed with water, then with a 10% NaOH solution, with water, then with a saturated sodium chloride solution, dried over magnesium sulfate and the solvent was vacuum evaporated. The residue was chromatographed on silica, eluting with a DCM/MeOH (90/10; v/v) mixture. 13.4 g of the expected product was obtained which was used as such in the following step.

h) N-[2-(3,4-dichlorophenyl)-4-hydroxybutyl]-N-methyl(3-isopropoxyphenyl)acetamide Several drops of a saturated solution of hydrochloric acid in ether was added to a solution of 13.4 g of the compound obtained from the preceding step in 200 ml of MeOH and stirred for 1 hour at RT. The reaction mixture was vacuum concentrated, the residue was taken up in MeOH and vacuum evaporated. 11.70 g of the expected product was obtained which was used as such in the following step.

i) N-[2-(3,4-dichlorophenyl)-4-(methanesulfonyloxy)butyl]-N-methyl(3-isopropoxyphenyl)acetamide 6.68 g of triethylamine was added to a solution of 11.70 g of the compound obtained from the preceding step in 100 ml of DCM followed by dropwise addition of a solution of 6.94 g of methanesulfonyl chloride in 30 ml of DCM. The reaction mixture was stirred for 6 hours at RT then vacuum concentrated. The residue was extracted with EtOAc, washed with water, then with a saturated sodium chloride solution, dried over magnesium sulfate then the solvent was vacuum evaporated. The residue was chromatographed on silica, eluting with a DCM/MeOH (99/1; v/v) mixture. 13.04 g of the expected product was obtained as an oil.

NMR spectrum at 200 MHz in DMSO.

1.3 ppm: d: 6H 2.05 ppm: mult: 2H 2.8 ppm:sd: 3H 3 to 4.3 ppm: m: 10H 4.6 ppm: sept: 1H 6.4 to 7.9 ppm: m: 7H Preparation 3

3-(3,4-dichlorophenyl)-3-[2-methanesulfonyloxy)ethyl]-1-[(3-isopropoxyphenyl) acetyl]piperidine a) Ethyl ester of 4-(3,4-dichlorophenyl)-4-cyano-6-(tetrahydropyran-2-yloxy) hexanoic acid A solution of 0.067 mole of lithium diisopropylamide in 100 ml of THF was added dropwise to a solution of 21 g of the compound obtained from step a) of Preparation 2 in 100 ml of THF and stirred for 1 hour at RT. 12 g of ethyl 3-bromopropionate was added and the reaction mixture was heated at 50° C. for 2 hours. After cooling, the reaction mixture was poured into a saturated ammonium chloride solution, extracted with ether, washed with water, dried over sodium sulfate and the solvent was vacuum evaporated. The residue was chromatographed on silica, eluting with a DCM/EtOAc (100/1; v/v) mixture. 13 g of the expected product was obtained which was used as such in the following step.

b) 5-(3,4-dichlorophenyl)-5-[2-(tetrahydropyran-2-yloxy)ethyl]piperidine-2-one 40 ml of concentrated ammonia was added to a solution of 13 g of the compound obtained from the preceding step in 250 ml of EtOH, then Raney nickel was introduced (10% of the quantity of the starting nitrile). Hydrogenation was then carried out at RT and at atmospheric pressure. The catalyst was filtered through Celite and the filtrate was vacuum evaporated. The residue was taken up in water, extracted with ether, washed with water, dried over magnesium sulfate and the solvent was vacuum evaporated. 9 g of the expected product was obtained which was used as such in the following step.

c) 3-(3,4-dichlorophenyl)-3-[2-(tetrahydropyran-2-yloxy)ethyl]piperidine 3.9 g of the compound obtained from the preceding step in 50 ml of THF was added to a suspension of 0.9 g of lithium aluminium hydride in 5 ml of THF heated to 60° C. The reaction mixture was stirred for 1 hour at 60° C. After cooling, 1 ml of water was added, then 1 ml of 4N NaOH then 3 ml of water. The mineral salts were filtered through Celite, the filtrate was decanted and the organic phase was vacuum evaporated. The residue was taken up in ether, dried over magnesium sulfate and the solvent was vacuum evaporated. 3.4 g of the expected product was obtained which was used as such in the following step.

d) 3-(3,4-dichlorophenyl)-3-[2-(tetrahydropyran-2-yloxy)ethyl]-1-(3-isopropoxyphenyl)acetylpiperdine 5.9 g of 3-isopropoxyphenylacetic acid and 21.6 g of BOP was added to a solution of 17.5 g of the compound obtained from the preceding step in 100 ml of DCM. The reaction mixture was stirred for 1 hour at RT then vacuum concentrated. The residue was taken up in EtOAc, washed with water, then with a 10% NaOH solution, with water, with a buffer solution with pH =2, then with a saturated sodium chloride solution, dried over sodium sulfate and the solvent was vacuum evaporated. The residue was chromatographed on silica, eluting with DCM then with a gradient of a mixture of DCM/EtOAc from (99/1; v/v) to (75/25; v/v). 21.5 g of the expected product was obtained which was used as such in the following step.

e) 3-(3,4-dichlorophenyl)-3-(2-hydroxyethyl)-1-(3-isopropoxyphenyl) acetylpiperidine A mixture of 21.5 g of the compound obtained from the preceding step, 0.2 g of Amberlyst 15, and 75 ml of MeOH was refluxed for 4 hours. The reaction mixture was filtered through Celite and the filtrate was vacuum evaporated. 18.2 g of the expected product was obtained which was directly used in the following step without purification.

f) 3-(3,4-dichlorophenyl)-3-[2-(methanesulfonyloxy)ethyl]-1-[(3-isopropoxyphenyl)acetyl]piperidine 4.4 g of triethylamine was added to a solution of 18.2 g of the compound obtained from the preceding step in 75 ml of DCM, cooled to 0° C., followed by dropwise addition of a solution of 4.4 g of methanesulfonyl chloride in 20 ml of DCM. The reaction mixture was stirred for 1 hour then vacuum concentrated. The residue was taken up in ether, washed with water, dried over sodium sulfate and the solvent was vacuum evaporated. 20 g of the expected product was obtained as an oil.

NMR spectrum at 200 MHz in DMSO.

0.8 to 2.4 ppm: m: 12H
3.1 ppm: s: 3H
3.1 to 4.8 ppm: m: 9H
6.5 to 7.9 ppm: m: 7H

EXAMPLE 1

1-[3-(3,4-dichlorophenyl)-4-[N-methyl-(3-isopropoxy-phenyl)-acetylamino]butyl]-4-phenylpyridinium chloride hemihydrate

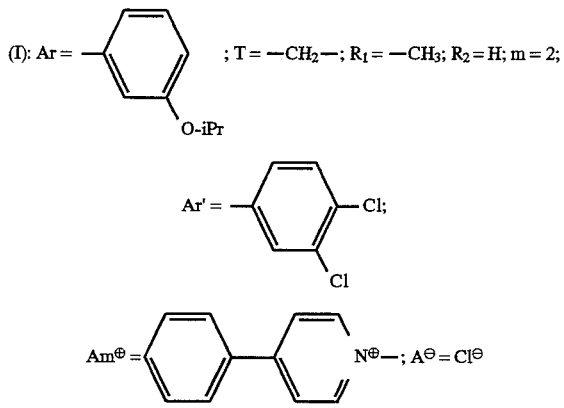

(I): Ar = (3-isopropoxyphenyl); T = —CH$_2$—; R$_1$ = —CH$_3$; R$_2$ = H; m = 2;

Ar' = (3,4-dichlorophenyl);

Am$^\oplus$ = (4-phenylpyridinium); N$^\oplus$—; A$^\ominus$ = Cl$^\ominus$

A mixture of 2.47 g of 4-phenylpyridine, 2 g of the compound obtained from Preparation 2 and 10 ml of acetonitrile was refluxed for 7 hours 30 minutes. The reaction mixture was vacuum concentrated and the residue was washed three times with ether to eliminate excess 4-phenylpyridine. After the final decanting operation, the residue was dissolved in DCM, the organic phase was washed three times with a saturated sodium chloride solution (to exchange the methanesulfonate anion for the chloride anion), dried over sodium sulfate and the solvent was vacuum evaporated. It was chromatographed on silica, eluting with a gradient of a DCM/MeOH (95/5; v/v) mixture. 1.45 g of the expected product was obtained after crystallization from ether. MP =108°–110° C.

EXAMPLE 2

4-benzyl-1-[3-(3,4-dichlorophenyl)-4)-4-[N-methyl-(3-iso-propyloxyphenyl) acetylamino]butyl] pyridinium methanesulfonate dihydrate.

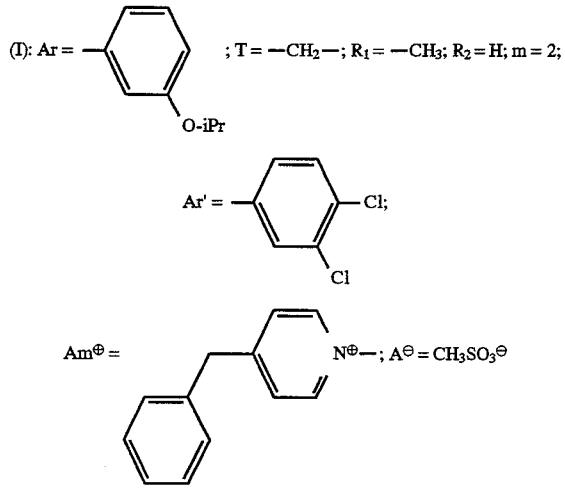

(I): Ar = (3-isopropoxyphenyl); T = —CH$_2$—; R$_1$ = —CH$_3$; R$_2$ = H; m = 2;

Ar' = (3,4-dichlorophenyl);

Am$^\oplus$ = (4-benzylpyridinium); N$^\oplus$—; A$^\ominus$ = CH$_3$SO$_3$$^\ominus$ A mixture of 1 g of 4-benzylpyridine, 1 g of the compound obtained from Preparation 2 and 5 ml of acetonitrile was refluxed for 10 hours. The reaction mixture was vacuum evaporated and the residue was chromatographed on silica, eluting with a DCM/MeOH (90/10; v/v) mixture. 0.38 g of the expected product was obtained after triturating in ether and filtering off. MP =66°–68° C.

EXAMPLE 3

1-[2-[3-(3,4-dichlorophenyl)-1-[(3-isopropoxy-phenyl) acetyl]-piperidin-3-yl]ethyl]-4-phenylpyridinium chloride 1,5 hydrate

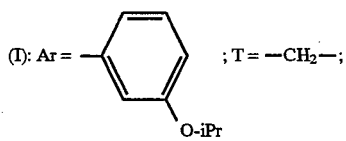

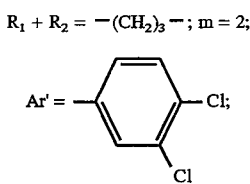

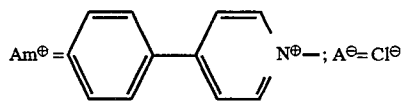

A mixture of 2.33 g of 4-phenylpyridine, 2 g of the compound obtained from Preparation 3 and 10 ml of acetonitrile was refluxed for 9 hours 30 minutes. The reaction mixture was vacuum evaporated and the residue was washed three times with ether. After the final decanting operation, the residue was dissolved in DCM, a saturated sodium chloride solution was added and the mixture was stirred overnight. After decanting, the organic phase was washed twice with a saturated sodium chloride solution, dried over sodium sulfate and the solvent was vacuum evaporated. The residue was chromatographed on silica, eluting with a gradient of a DCM/MeOH mixture (98/2; v/v) to (95/5; v/v). 1.49 g of the expected product was obtained after crystallization from a DCM/ether mixture. MP=130°–132° C.

EXAMPLE 4

4-benzyl-1-[2-[3-(3,4-dichlorophenyl)-1-[(3-isopropoxyphenyl)-acetyl]piperidin-3-yl]ethyl] pyridinium chloride dihydrate

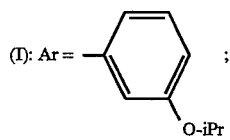

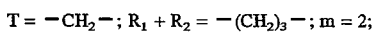

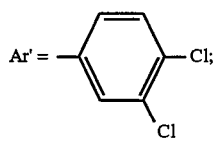

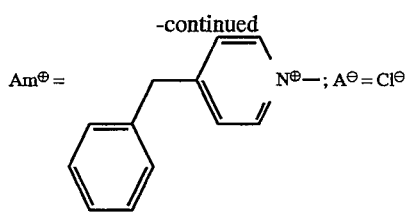

A mixture of 1.4 g of 4-phenylpyridine, 1.1 g of the compound obtained from Preparation 3 and 10 ml of acetonitrile was refluxed for 11 hours 30 minutes. The reaction mixture was vacuum evaporated and the residue was washed three times with ether. After the final decanting operation, the residue was dissolved in DCM, the organic phase was washed three times with a saturated sodium chloride solution, dried over sodium sulfate and the solvent was vacuum evaporated. The residue was chromatographed on silica, eluting with a gradient of a DCM/MeOH mixture (95/5; v/v) to (90/10; v/v). 0.33 g of the expected product was obtained after crystallisation from ether. MP=103°–105° C.

We claim:

1. A compound of formula

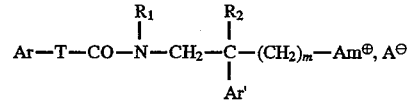

(I)

in which:

Ar represents an aromatic or heteroaromatic mono-, di- or tricyclic group which may be substituted;

T represents a direct bond; a hydroxymethylene group; a $(C_1-C_4)$alkoxymethylene group; a $(C_1-C_5)$alkylene group; an oxygen atom; a —$NR_3$ group; a vinylene group;

Ar' represents phenyl which may be unsubstituted or substituted one or more times by a substituent selected from: a halogen atom, trifluoromethyl, hydroxy, $(C_1-C_4)$alkoxy, $(C_1-C_4)$alkyl, said substituents being identical or different; thienyl; benzothienyl; naphthyl; indolyl which may be N-substituted by a $(C_1-C_4)$alkyl or benzyl;

$R_1$ represents hydrogen; $(C_1-C_4)$alkyl; ω-hydroxy-$(C_2-C_4)$alkylene; ω-$(C_1-C_4)$alkoxy-$(C_2-C_4)$alkylene; ω-benzyloxy-$(C_2-C_4)$alkylene; ω-formyloxy-$(C_2-C_4)$ alkylene; ω-$(C_1-C_4)$alkylcarbonyloxy-$(C_2-C_4)$ alkylene; ω-benzoyloxy-$(C_2-C_4)$alkylene; ω-$R_6$NHCOO—$(C_2-C_4)$alkylene; ω-$(C_1-C_4)$alkylthio-$(C_2-C_4)$alkylene; ω-carboxy-$(C_2-C_4)$alkylene; ω-$(C_1-C_4)$alkoxycarbonyl-$(C_2-C_4)$alkylene; ω-$R_7R_8$NCO—$(C_2-C_4)$alkylene; ω-$R_9R_{10}$N—$(C_2-C_4)$ alkylene; ω-$R_{11}$CONR$_{12}$—$(C_2-C_4)$alkylene; ω-$R_{13}$OCONR$_{12}$—$(C_2-C_4)$alkylene; ω-$R_7R_8$NCONR$_{12}$—$(C_2-C_4)$alkylene; ω-$R_{14}$SO$_2$NR$_{12}$—$(C_2-C_4)$ alkylene; ω-$(C_1-C_4)$ alkylcarbonyl-$(C_2-C_4)$alkylene; ω-cyano-$(C_1-C_3)$ alkylene;

$R_2$ represents hydrogen;

or $R_1$ and $R_2$ together form a 1,2-ethylene, 1,3-propylene or 1,4-butylene group;

$R_3$ represents hydrogen or $(C_1-C_4)$alkyl;

$Am^+$ represents a substituted 1-pyridylium radical of formula:

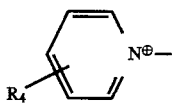

$R_4$ represents a group:

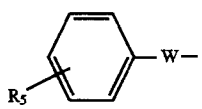

W represents a direct bond; a methylene group; an oxygen atom; a sulfur atom; a —$NR_3$—group;

$R_5$ represents hydrogen; a halogen; hydroxy; $(C_1-C_4)$ alkoxy; $(C_1-C_4)$alkyl; trifluoromethyl;

$R_6$ represents $(C_1-C_7)$alkyl or phenyl;

$R_7$ and $R_8$ each independently represent hydrogen or $(C_1-C_7)$alkyl; $R_8$ may also represent $(C_3-C_7)$ cycloalkyl, $(C_3-C_7)$cycloalkylmethyl, phenyl or benzyl;

or $R_7$ and $R_8$ together with the nitrogen atom to which they are bound constitute a heterocycle selected from azetidine, pyrrolidine, piperidine, morpholine, thiomorpholine or perhydroazepine;

$R_9$ and $R_{10}$ each independently represent hydrogen or a $(C_1-C_7)$alkyl; $R_{10}$ may also represent $(C_3-C_7)$ cycloalkyl-methyl or benzyl;

$R_{11}$ represents hydrogen, $(C_1-C_7)$alkyl, vinyl, phenyl, benzyl, pyridyl or $(C_3-C_7)$cycloalkyl which may be unsubstituted or substituted by one or more methyl groups;

$R_{12}$ represents hydrogen or $(C_1-C_7)$alkyl;

$R_{13}$ represents $(C_1-C_7)$alkyl or phenyl;

$R_{14}$ represents $(C_1-C_7)$alkyl; a free amino group or an amino group substituted by one or two $(C_1-C_7)$alkyls; phenyl which may be unsubstituted or substituted one or more times by a substituent selected from: a halogen atom, $(C_1-C_7)$alkyl, trifluoromethyl, hydroxy, $(C_1-C_7)$ alkoxy, carboxy, $(C_1-C_7)$alkoxycarbonyl, $(C_1-C_7)$ alkylcarbonyloxy, cyano, nitro, a free amino group or an amino group substituted by one or two $(C_1-C_7)$ alkyls, said substituents being identical or different;

m is 2 or 3;

$A^-$ is an anion;

and its salts with mineral or organic acids, in an optically pure or a racemic form.

2. A compound of formula (I) according to claim 1, in which:

Ar represents:
phenyl which may be unsubstituted or substituted one or more times by a substituent selected from: a halogen atom; trifluoromethyl; cyano; hydroxy; nitro; amino which may be unsubstituted or substituted one or more times by $(C_1-C_4)$alkyl; benzylamino; carboxy; $(C_1-C_{10})$alkyl; $(C_3-C_8)$cycloalkyl which may be unsubstituted or substituted one or more times by methyl; $(C_1-C_{10})$alkoxy; $(C_3-C_8)$ cycloalkyloxy which may be unsubstituted or substituted one or more times by methyl; mercapto; $(C_1-C_{10})$alkylthio; formyloxy; $(C_1-C_6)$ alkylcarbonyloxy; formylamino; $(C_1-C_6)$ alkylcarbonylamino; benzoylamino; $(C_1-C_4)$ alkoxycarbonyl; $(C_3-C_7)$cycloalkyloxycarbonyl; carbamoyl which may be unsubstituted or substituted one or more times by $(C_1-C_4)$alkyl; ureido which may be unsubstituted or substituted one or more times in the 3 position by $(C_1-C_4)$alkyl or $(C_3-C_7)$cycloalkyl; (pyrrolidin-1-yl)carbonylamino, the substituents being identical or different;

naphthyl which may be unsubstituted or substituted one or more times by a halogen, trifluoromethyl, $(C_1-C_4)$ alkyl, hydroxy, $(C_1-C_4)$alkoxy;

pyridyl; thienyl; indolyl; quinolyl; benzothienyl; imidazolyl;

and its salts with mineral or organic acids.

3. A compound according to claim 1, in which:

$R_4$ is an unsubstituted phenyl group or an unsubstituted benzyl group;

and its salts with mineral or organic acids.

4. A compound according to claim 1, of formula:

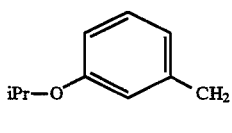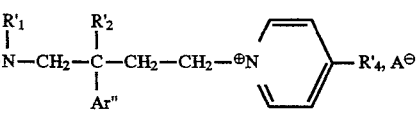

(I')

where iPr represents the isopropyl radical; Ar" represents 3,4-dichlorophenyl or 3,4-difluorophenyl; $R'_1$ and $R'_2$ respectively represent a methyl group and hydrogen, a 2-acetoxyethyl group and hydrogen, a 2-hydroxyethyl group and hydrogen, or together they form a 1,3-propylene group; $R'_4$ is a phenyl or benzyl group and $A^-$ is a pharmaceutically acceptable anion.

5. A compound according to claim 1, selected from:

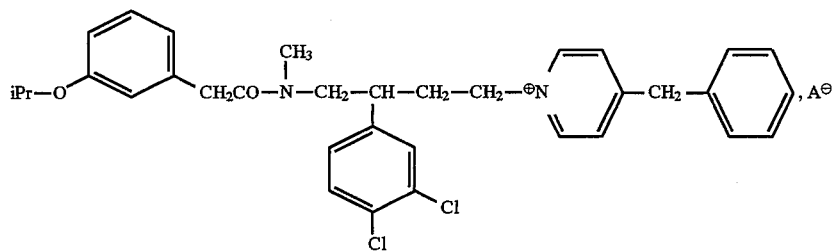

(I'')

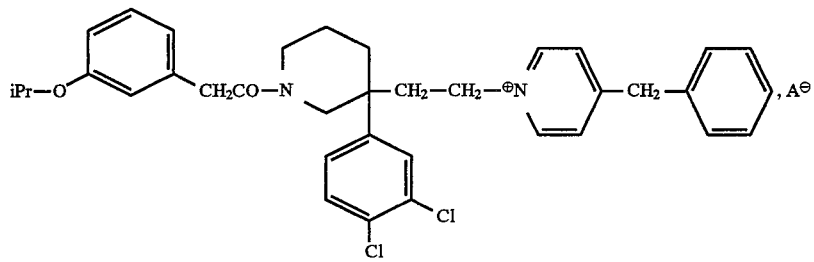

(I''')

in which $A^-$ is a pharmaceutically acceptable anion.

6. A compound according to claim 1, characterized in that $A^-$ is an anion selected from chloride, bromide, iodide, hydrogensulfate, methanesulfonate, para-toluenesulfonate, acetate and benzenesulfonate.

7. A process for the preparation of compounds of formula (I) in accordance with claim 1, characterized in that a derivative of the following formula:

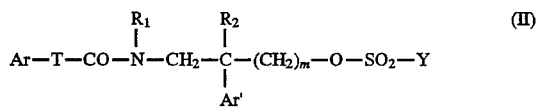

(II)

in which Y represents a methyl, phenyl, tolyl, or trifluoromethyl group and m, Ar, T, $R_1$, $R_2$ and Ar' are as defined in claim 1 for (I), provided that when $R_1$ represents a ω-hydroxy-$(C_2-C_4)$alkylene group, the hydroxy group is protected, and when $R_1$ represents a ω-amino-$(C_2-C_4)$alkylene group, the amino group is protected, is treated by an aromatic heterocycle of formula (III):

Am (III)

in which Am represents pyridine substituted by $R_4$, and $R_4$ is as defined above in claim 1 for (I), in an organic solvent at a temperature of between room temperature and 120° C. and, after any necessary deprotection of the hydroxy group or the amino group, the salt obtained is isolated in the form of a sulfonate, or the sulfonate anion ($YSO_3$—) of the salt obtained is exchanged with another anion and optically pure isomers are optionally separated.

8. A pharmaceutical composition containing a compound of formula (I) according to claim 1 as an active ingredient.

9. A pharmaceutical composition according to claim 8, in a unit dose, in which the active ingredient is mixed with at least one pharmaceutical excipient.

10. A composition according to claim 9, containing 0.5 mg to 1000 mg of active ingredient.

11. A composition according to claim 10, containing 2.5 mg to 250 mg of active ingredient.

* * * * *